(12) United States Patent
Kliuchnikov et al.

(10) Patent No.: US 11,188,842 B2
(45) Date of Patent: Nov. 30, 2021

(54) METHODS FOR OBTAINING SOLUTIONS TO MULTIPRODUCT FORMULAS

(71) Applicant: Microsoft Technology Licensing, LLC, Redmond, WA (US)

(72) Inventors: Vadym Kliuchnikov, Redmond, WA (US); Guang Hao Low, Singapore (SG); Nathan Wiebe, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 236 days.

(21) Appl. No.: 16/442,048

(22) Filed: Jun. 14, 2019

(65) Prior Publication Data

US 2020/0394545 A1    Dec. 17, 2020

(51) Int. Cl.
*G06N 10/00*     (2019.01)
*G06F 17/12*     (2006.01)
*G06F 17/16*     (2006.01)

(52) U.S. Cl.
CPC ............. *G06N 10/00* (2019.01); *G06F 17/12* (2013.01); *G06F 17/16* (2013.01)

(58) Field of Classification Search
CPC .......... G06N 10/00; G06F 17/12; G06F 17/16
USPC ........................................................ 708/620
See application file for complete search history.

(56) References Cited

PUBLICATIONS

Aharonov, et al., "Adiabatic Quantum State Generation and Statistical Zero Knowledge", In Proceedings of the Thirty-Fifth Annual ACM Symposium on Theory of Computing., Jun. 9, 2003, pp. 20-29.

Bardeen, et al., "Theory of Superconductivity", In Journal of Physical review, vol. 108, Issue 5, Dec. 1, 1957, pp. 1175-1204.

Berry, et al., "Black-box Hamiltonian simulation and unitary implementation", In Journal Quantum Information and Computation, vol. 12 Issue 1-2, Jan. 2012, pp. 29-62.

Berry, et al., "Efficient Quantum Algorithms for Simulating Sparse Hamiltonians", In Journal of Communications in Mathematical Physics, vol. 270, Issue 2, Mar. 1, 2007, 09 Pages.

(Continued)

*Primary Examiner* — Tan V Mai
(74) *Attorney, Agent, or Firm* — Alleman Hall Creasman & Tuttle LLP

(57) ABSTRACT

Examples are disclosed relating to obtaining a solution to a multiproduct formula of order m to solve a quantum computing problem comprising a product formula. One example provides a method comprising selecting a set of exponents $k_j$, wherein each $k_j$ is a real number and is an exponent in a linear combination of product formulas. Based on the set of exponents $k_j$, a set of pre-factors $a_j$ is determined based on an underdetermined solution to an m×M system of linear equations, where M is a number of lower-order product formulas in the linear combination of product formulas. The set of exponents $k_j$ and the set of pre-factors $a_j$ are used to solve the quantum computing problem comprising the product formula. By minimizing the set of exponents $k_j$ and the set of pre-factors $a_j$, sparse solutions to the multiproduct formula are generated, reducing computational time and scaling.

20 Claims, 5 Drawing Sheets

(56) References Cited

PUBLICATIONS

Berry, et al., "Exponential Improvement in Precision for Simulating Sparse Hamiltonians", In Proceedings of the ACM Symposium on Theory of Computing, May 31, 2014, 10 Pages.

Berry, et al., "Hamiltonian Simulation with Nearly Optimal Dependence on all Parameters", In Proceedings of IEEE 56th Annual Symposium on Foundations of Computer Science, Oct. 17, 2015, pp. 792-809.

Berry, et al., "Simulating Hamiltonian Dynamics With a Truncated Taylor Series", In Journal of Physical Review Letters, vol. 114, Issue 9, Mar. 3, 2015, 5 Pages.

Blanes, et al., "Improved High Order Integrators Based on the Magnus Expansion", In Journal of BIT Numerical Mathematics, vol. 40, Issue 3, Sep. 1, 2000, 18 Pages.

Campbell, Earl, "A Random Compiler for Fast Hamiltonian Simulation", In Repository of arXiv:1811.08017, Nov. 19, 2018, pp. 1-7.

Childs, et al., "Faster Quantum Simulation by Randomization", In Repository of arXiv:1805.08385, May 22, 2018, pp. 1-19.

Childs, et al., "Hamiltonian Simulation Using Linear Combinations of Unitary Operations", In Proceedings of Quantum Information and Computation, vol. 12, Issue 11-12, Nov. 2012, 18 Pages.

Childs, et al., "Nearly Optimal Lattice Simulation by Product Formulas", In Repository of arXiv:1901.00564, Jan. 3, 2019, pp. 1-41.

Childs, et al., "Toward the first quantum simulation with quantum speedup", In Proceedings of the National Academy of Sciences, vol. 115, Issue 38, Sep. 18, 2018, pp. 9456-9461.

Chin, Siu A.., "Multi-Product Splitting and Runge-Kutta-Nystrom Integrators", In Journal of Celestial Mechanics and Dynamical Astronomy, vol. 106, Issue 4, Mar. 11, 2010, pp. 391-406.

Feynman, Richard P.., "Simulating Physics with Computers", In International Journal of Theoretical Physics, vol. 21, Issue 6, Jun. 1, 1982, pp. 467-477.

Gilyen, et al., "Quantum Singular Value Transformation and Beyond: Exponential Improvements for Quantum Matrix Arithmetics", In Repository of arXiv:1806.01838, Jun. 6, 2018, 67 Pages.

Haah, et al., "Quantum Algorithm for Simulating Real Time Evolution of Lattice Hamiltonians", In Proceedings of 59th Annual Symposium on Foundations of Computer Science, Oct. 7, 2018, pp. 350-360.

Jordan, et al., "Quantum Algorithms for Quantum Field Theories", In Journal of Science, vol. 336, Issue 6085, Jun. 1, 2016, pp. 1130-1133.

Lloyd, Seth, "Universal Quantum Simulators", In the Journal of Science, vol. 273, Issue 5278, Aug. 23, 1996, pp. 1073-1078.

Low, et al., "Hamiltonian Simulation by Qubitization", In Repository of arXiv:1610.06546, Oct. 21, 2016, 19 Pages.

Low, et al., "Hamiltonian Simulation by Uniform Spectral Ampli?cation", In Repository of arXiv:1707.05391, Jul. 19, 2017, 32 Pages.

Low, et al., "Methodology of Resonant Equiangular Composite Quantum Gates", In Journal of Physical Review X, vol. 6, Issue 4, Dec. 28, 2016, pp. 1-13.

Low, et al., "Optimal Hamiltonian Simulation by Quantum Signal Processing", In Journal of Physical Review Letters, vol. 118, Issue 1, Jan. 5, 2017, pp. 1-6.

O'Malley, et al., "Scalable quantum simulation of molecular energies", In Journal of Physical Review X, vol. 6, Issue 3, Jul. 18, 2016, pp. 1-13.

Poulin, et al., "The Trotter Step Size Required for Accurate Quantum Simulation of Quantum Chemistry", In Journal of Quantum Information and Computation, vol. 15 Issue 5-6, Apr. 1, 2015, 13 Pages.

Rudelson, et al., "Sparse Reconstruction by Convex Relaxation: Fourier and Gaussian Measurements", In Proceedings of 40th Annual Conference on Information Sciences and Systems, Mar. 22, 2006, pp. 207-212.

Suzuki, Masuo, "Fractal Decomposition of Exponential Operators with Applications to Many-Body Theories and Monte Carlo Simulations", in Journal of Physics Letters A, vol. 146, Issue 6, Jun. 4, 1990.

Trotter, H. F., "On the Product of Semi-Groups of Operators", In Proceedings of American Mathematical Society, vol. 10, Issue 4, Aug. 1, 1959, pp. 545-551.

Whitfield, et al., "Simulation of Electronic Structure Hamiltonians using Quantum Computers", In Journal of Molecular Physics, vol. 109, Issue 5, Mar. 10, 2011, pp. 735-750.

Childs, et al., "Hamiltonian Simulatfon Using Linear Combinations of Unitary Operation", In Repository of arXiv:1202.5822, Feb. 27, 2012, 18 Pages.

Geiser, et al., "Multi-product expansion, Suzuki's method and the Magnus integrator for solving time-dependent problems", Retrieved from: https://www.researchgate.net/publication/228653169_Multi-product_expansion_Suzuki's_method_and_the_Magnus_integrator_for_solving_time-dependent_problems, Sep. 2011, 19 Pages.

Hedemann, et al., "Explicit Inverse Confluent Vandermonde Matrices with Applications to Exponential Quantum Operators", In Repository of arXiv:1709.05257, Sep. 14, 2017, 9 Pages.

Kivlichan, et al., "Bounding the Costs of Quantum Simulation of many-body Physics in Real Space", In Journal of Journal of Physics A: Mathematical and Theoretical, vol. 50, Issue 30, Jun. 29, 2017, 32 Pages.

Low, et al., "Well-conditioned Multi Product Hamiltonian simulation", In Repository of arXiv: 1907.11679, Jul. 26, 2019, 9 Pages.

"International Search Report and Written Opinion Issued in PCT Application No. PCT/US2020/030046", dated Aug. 13, 2020, 14 Pages.

METHODS FOR OBTAINING SOLUTIONS TO MULTIPRODUCT FORMULAS

BACKGROUND

Simulating chemical systems may be used to reduce trial and error losses by predicting the properties of chemicals and expected outcomes of reactions. As quantum computers are based on quantum mechanics, quantum simulations may be used to natively simulate the behavior of electrons, atoms, and/or molecules in a system, more efficiently than can classical computing systems. Rather than consuming computational resources exponentially (e.g., $2^n$ for an n electron system), quantum computers may only use polynomially many resources. This allows for the simulation of larger systems without relying on approximations that reduce the accuracy of resulting predictions.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

In one disclosed example, a method for obtaining a solution to a multiproduct formula of order m to solve a quantum computing problem comprising a product formula. One example provides a method comprising selecting a set of exponents $k_j$, wherein each $k_j$ is a real number and is an exponent in a linear combination of product formulas. Based on the set of exponents $k_j$, a set of pre-factors $a_j$ is determined based on an underdetermined solution to an m×M system of linear equations, where M is a number of lower-order product formulas in the linear combination of product formulas. The set of exponents $k_j$ and the set of pre-factors $a_j$ are used to solve the quantum computing problem comprising the product formula. By minimizing the set of exponents $k_j$ and the set of pre-factors $a_j$, sparse solutions to the multiproduct formula are generated, reducing computational time and scaling.

DETAILED DESCRIPTION

Figure 1:
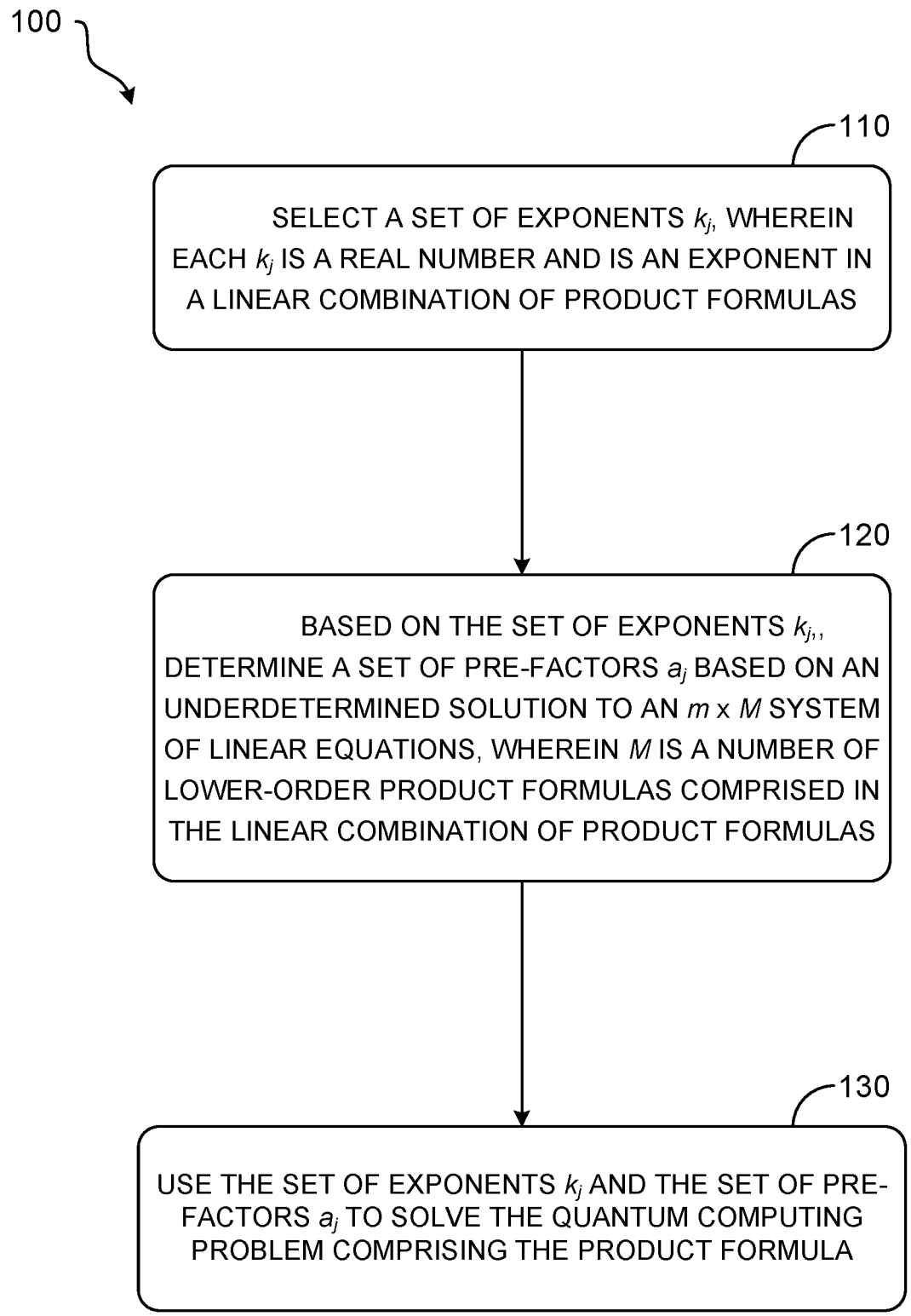
FIG. 1 shows an example method for obtaining a solution to a multiproduct formula of order m to solve a quantum computing problem comprising a product formula.

The curse of dimensionality underlies the difficulty of simulating quantum systems. As the Hilbert space dimension grows exponentially with particle number, classical computers require exponential time to accurately reproduce quantum dynamics. Fortunately, quantum computers show great promise in resolving this conundrum.

Many physical systems of interest, such as in superconductivity, chemistry, and general quantum field theories, are described by Hamiltonians $H=\Sigma_{j=1}^{N}h_j$ that are a sum of polynomially many N local terms. Even though each term modifies exponentially many amplitudes in the wavefunction, quantum computers may nevertheless apply time-evolution by each with a polynomial amount of physical resources.

A series of quantum gates may be generated that approximate the time-evolution of a Hamiltonian. Such time-evolution operators may be invoked as subroutines in additional quantum algorithms. For example, quantum algorithms may be used for factoring large numbers, which is important in many cryptography applications.

Just as there are many algorithms to multiply numbers or matrixes together, there are also many ways to design a quantum circuit that implements this time evolution operator. All of these different algorithms have various trade-offs, unique strengths and unique weaknesses. Some of them target special structures of the problems that are being simulated, others target different problems or structure types.

There is often a trade-off between the cost and complexity of implementing an algorithm. For example, to multiply two matrixes of dimension n×n, the traditional method has a complexity of $n^3$. The best possible order for this operation has a complexity of $n^{2.3}$. However, this algorithm is somewhat impractical because there exists a large constant factor that is applied to n. There exists much interest in designing quantum systems that operate more efficiently on a quantum computer. Improvements come both in terms of reducing exponents and in reducing the value of the constant factors. In most of these cases performance of the implementation can be quantified in terms of scaling with respect to time, number of terms, and target error of the simulation, as well as whether the exponents on these terms become smaller.

Early quantum simulation algorithms were based on an idea called Trotterization. To simulate a Hamiltonian that is the sum of many terms, the time-evolution for this Hamiltonian can be approximated by applying time-evolution to each term in sequence. Such quantum simulations may be efficiently performed on a quantum computer, e.g., in polynomial time and polynomial cost with respect to both the number of terms, and the target error.

However, Hamiltonians and other physical systems are described by more parameters than just time and number of terms. For example, given a system with two molecules that are far away from each other, it can be assumed that the two molecules do not interact with each other. As such, the cost of simulating these two pseudo-independent molecules should just be twice the cost of simulating one molecule. The cost of simulating n molecules should scale linearly with n. However, the most generic quantum simulation algorithms actually scale quadratically with respect to the number of terms n, because the structure of distance between terms is not introduced. For Hamiltonians, these algorithms assume the worst-case scenario, e.g., that every term can interact with every other term. Thus, simulation costs are based on the number of pair-wise interactions ($n^2$). These types of structures in real systems are important and common but may not be exploited by the most generic quantum simulation algorithms.

Trotterization and subsequent variations (e.g., Trotter-Suzuki product formulas), take into account a very common type of structure and are of interest due to their simplicity and low space requirements. As an example, they may exploit how many terms in a Hamiltonian might commute with each other. This leads to far superior empirical performance on typical quantum systems than predicted by rigorous, but extremely loose upper bounds. The terms only interact with neighboring terms, rather than all terms, thus considering both strong and weak interactions based on inter-term distance. Thus, performing these simulations using a product formula simulation algorithm reduces the cost significantly compared with using the worst-case bounds.

At first order, time-evolution by the Hamiltonian is approximated by sequentially evolving by its parts, that is $\vec{U}_1(\Delta) = \vec{\prod}_{j=1}^{N} e^{-ih_j\Delta} = e^{-iH\Delta} + \mathcal{O}(\Sigma_{j<k}\|[h_j, h_k]\|\Delta^2)$. Thus evolution $e^{-iHt}$ for arbitrary long times t is accomplished by applying t/Δ approximate segments, each comprising of N exponentials, with Δ chosen to control the overall simulation error. Higher order variants achieve better scaling, and rigorous bounds place the number of exponentials required using an order m integrator at $\leq 2N5^m(N \max_j\|h_j\|t)^{1+1/m}/\epsilon^{1/m}$. Due to its simplicity, this approach has been realized in experiments, and may even find useful applications in the near-term where decoherence still severely limits the number of quantum gates applied.

Ultimate limits on the performance of Hamiltonian simulation may be obtained by reducing worst-case computational problems to physical simulations. As these bounds indicate that the scaling should be strictly linear in time and logarithmic in error like $$\Omega\left(t + \frac{\log(1/\epsilon)}{\log\log(1/\epsilon)}\right),$$

the polynomial gap between this and any product formula has ignited a flurry of post-Trotter simulation algorithms. These are based on different paradigms such as quantum walks, linear-combination-of-unitaries, qubitization, and quantum signal processing, and can match this lower bound with respect to all parameters.

In practice, product formula approaches are simulated for small systems, then extrapolated to larger systems. However, while such Trotter-Suzuki product formulas represent an improvement, they still have limitations, particularly at simulating worst-case problems.

Multi-product formulas were developed as an attempt to deal with many of the drawbacks of Trotter-Suzuki formulas for solving certain classes of differential equations. The principal idea behind them is to use a linear combination of Trotter formulas to construct a new integrator for a quantum system. However, most multi-product formulas are ill-conditioned, requiring precise cancellation of terms to generate plausible solutions.

For a quantum circuit that implements the time-evolution operator for a time (t), the number of quantum gates needed to apply for worst-case algorithms scales linearly in time. The scaling with respect to error is logarithmic, and the scaling with respect to the number of terms is quadratic. The simplest product formulas (e.g., first-order) have quadratic scaling in time, cubic scaling with respect to number of terms, and logarithmic scaling on error (e.g., 1/error). If the same product formula is used for a longer time, the errors sum, yielding a larger error that scales with simulation time. As the order of the product formula increases, the exponents on time and error also increase, with respect to the step size of the simulation. In other words, any order m product formula approximates real-time evolution for time t and error ε using a multiplicative factor $e^{o(m)}(t/\epsilon)^{o(1/m)}$ more exponentials than post-Trotter simulation algorithms that achieve an optimal worst-case scaling $\mathcal{O}(t+\log(1/\epsilon))$, but lose the ability to exploit commutativity of terms.

Applying very high order Trotter-Suzuki product formulas for these worst-case problems can yield almost linear scaling in time, almost quadratic scaling in number of terms, and almost logarithmic scaling with respect to error. This nearly matches that generic worst-case algorithms and should have better performance for these structured Hamiltonians.

However, there also exist constant pre-factors that are applied to scaling and cost exponents. Generic quantum simulation algorithms have optimal scaling in these parameters, and also have a very small constant factor for worst-case problems. First order product formulas have relatively poor scaling, but the constant factors are small. However, for the higher order Trotter-Suzuki product formulas, the constant factor grows exponentially with the order of the product formula. There is thus a threshold for the product formula order, above which the absolute time needed to run a simulation becomes unfeasibly large. In practice, due to this enormous pre-factor, greater than 4th order product formulas are rarely used.

Though product formulas are asymptotically suboptimal for worst-case problems, their constant factors are significantly smaller than rigorous bounds suggest. Indeed, numerical studies demonstrate that simulation errors are much smaller than expected if some Hamiltonian terms commute, to the point of providing an asymptotic advantage. A most dramatic separation in performance is observed in simulating geometrically local interactions, where even naive applications of product formulas have an almost-linear $\mathcal{O}(N^{1+o(1)})$ quantum gate cost in system size N. In contrast, post-Trotter simulation algorithms lose this desirable feature and, without highly specialized modifications, exhibit quadratic scaling $\Omega(N^2)$.

Indeed, commutating terms are common in typical quantum systems, which motivates continued interest in product formulas. One approach is based on multiproduct formulas, where a higher order 2m integrator is constructed from a linear combination of M≥m lower-order product formulas:

$$U_{\vec{k}}(\Delta) = \sum_{j=1}^{M} a_j U_2^{k_j}\left(\frac{\Delta}{k_j}\right) = e^{-iH\Delta} + \mathcal{O}((N\|h\|\Delta)^{2m+2}), \quad (1)$$

wherein U represents the product formula, M is a number of lower-order product formulas comprised in the linear combination of product formulas, Δ is a step size, $a_j$ is a set of pre-factors, H is a sum of Hamiltonians h, $\mathcal{O}$ is a cost function, and N is a number of terms. For example, if a product formula is raised to the power of exponent k, the product formula would be applied k times sequentially. The cost of taking a linear combination of product formulas scales with the pre-factor $a_j$. Error scales with the size of the Δ. In this example, there are M different product formulas, and thus M different step sized $$\left(\text{e.g., } \frac{\Delta}{k_j}\right).$$

In this example, there is a linear combination of these M different product formulas where each product formula is applied $k_j$ times according to that exponent's step size.

The linear combination of product formulas may be, for example the symmetric Trotter-Suzuki formula $U_2 (\Delta) = \vec{U}_1(\Delta/2) \cdot \vec{U}_1(\Delta/2) = e^{-iH\Delta} + O(\Delta^4)$, abbreviating $\|h\| = \max_j \|h\|_j$. With the simplest choice $k_j = j$ and $M = m$, only $\mathcal{O}(Nm^2)$ exponentials are required, which appears to be exponential improvement over the $e^{o(m)}(t/\epsilon)^{o(1/m)}$ ($N5^m$) required by Trotter-Suzuki formulas. Unfortunately, these multiproduct formulas are ill-conditioned—the coefficient (e.g., pre-factor) $a_m = e^{\Omega(m \log m)}$ grows exponentially with the order m. Thus, even the zeroth order constraint $\Sigma_{j=1}^m a_j = 1$ requires an extremely precise cancellation of terms. In the quantum setting, standard linear-combination-of-unitaries techniques translate this into an exponentially small success probability $\|\vec{a}\|_1^{-2}$.

Herein, a quantum algorithm for Hamiltonian simulations is presented that maintains the average-case characteristics of product formulas, while reducing the gap in worst-case gate complexity from polynomial in $t/\epsilon$ to logarithmic. This is achieved by solving the conditioning problem faced by multiproduct formulas. By solving for the required cancellations using an underdetermined system, sparse solutions are generated. Such a technique may be bootstrapped to any product formula, including for classical simulations, thus preserving commutativity of Hamiltonian terms.

The more general under-determined setting in Eq. (1) is considered where $M = m$, but $k_j$ can be arbitrary rather than an arithmetic sequence. The technical result of this solution is that for integers $k_j$ of size $\max_j |k_j| \in e^{o(m)}(t/\epsilon)^{o(1/m)}$ (m), well-conditioned solutions are generated to Eq. (1) where $\|\vec{a}\|_1 \in e^{o(m)}(t/\epsilon)^{o(1/m)}$ (log m) is exponentially smaller. This may allow for the generation and application of higher order, yet low-cost product formulas. In effect, this reduces the number of computing operations needed to solve a quantum computing application, such as the time-evolution of a Hamiltonian. Combined with oblivious amplitude amplification, this allows an order m integrator to be implemented deterministically with $e^{o(m)}(t/\epsilon)^{o(1/m)}$ (poly(m)) cost. Thus, overhead is reduced to just $\tilde{\mathcal{O}} \, m^2(t/\epsilon)^{o(1/m)}$, which translates into a worst-case gate complexity of $e^{o(m)}(t/\epsilon)^{o(1/m)}(t \log^{2+o(1)}(t/\epsilon))$ for Hamiltonian simulations.

FIG. 1 shows an example method 100 for obtaining a solution to a multiproduct formula of order m to solve a quantum computing problem comprising a product formula. Method 100 may be enacted via execution of stored instructions on a computing device. Such a computing device may be a quantum computing device and/or a classical computing device. An example quantum computing device is described herein and with regard to FIGS. 3 and 4, and an example classical computing device is described herein and with regard to FIG. 5.

At 110, method 100 includes selecting a set of exponents $k_j$, wherein each $k_j$ is a real number and is an exponent in a linear combination of product formulas. As an example, the linear combination of product formulas may be Eq (1).

wherein U represents the product formula, M is a number of lower-order product formulas comprised in the linear combination of product formulas, $\Delta$ is a step size, $a_j$ is a set of pre-factors, H is sum of Hamiltonians h, $e^{o(m)}(t/\epsilon)^{o(1/m)}$ is a cost function, N is a number of terms. For example, if a product formula is raised to the power of exponent k, the product formula would be applied k times sequentially. The cost of taking a linear combination of product formulas scales with the pre-factor $a_j$. Error scales with the size of the $\Delta$. In this example, there are M different product formulas, and thus M different step sized $$\left( e.g., \frac{\Delta}{k_j} \right).$$

In this example, there is a linear combination of these M different product formulas where each product formula is applied $k_j$ times according to that exponent's step size.

The cost of implementing this linear combination of product formulas scales with the one-norm of the prefactors and the sum of the exponents. Method 100 may be used to generate a scheme for obtaining a very general class of multi-product formulas, where the pre-factors are all small (e.g., polynomial in size, rather than exponentially large). Such product formulas may be referred to as "well-conditioned product formulas".

Theorem (Hamiltonian simulation by well-conditioned multiproduct formulas). There exists a quantum circuit based on multiproduct formulas $U_{\vec{k}}$ of the form in Eq. 1 that approximate the real-time evolution operator with error $\epsilon = \|U_{\vec{k}}(t) - e^{-it\Sigma_{j=1}^N h_j}\|$ using at most $$N_{exp} \leq 2Nt\lambda \|\vec{a}\|_1 \|\vec{k}\|_1 \left( \frac{8t\lambda \|\vec{a}\|_1}{\epsilon(2m+2)!} \right)^{\frac{1}{2m+1}} \quad (2)$$

exponentials, where $\lambda = \Sigma_{j=1}^N \|h_j\|$ and $\|\vec{a}\|_1 \|\vec{k}\|_1 \Theta \in (m^{2 \, \log^2}$ (m)). By minimizing cost with respect to m, $$N_{exp} \in e^{o(m)}(t/\epsilon)^{o(1/m)} (Nt\lambda \, \log^{2+o(1)}(t\lambda/\epsilon)). \quad (3)$$

Explicit constructions are also provided where $\|\hat{a}\|_1 \| \vec{k}\|_1 \approx 0.019 \, m^2 + 0.11 \log^2 m$).

Notably, this procedure may bootstrap off any product formula. Thus, it retains the product formula's desirable characteristics, and may similarly exhibit significantly better empirical performance than suggested by Theorem 1. For instance, Table 1 enumerates tighter bounds showing that $$N_{exp} \mathcal{O} \in \left( \max_{i,j,k} \|[h_i, [h_j, h_k]]\|^{O(1)} \right).$$

Multi-Product Formulas

Any symmetric product formula that approximates the time-evolution operator to at least leading order has the expansion $$U_2(\Delta) = e^{-iH\Delta + E_3 \Delta^3 + E_5 \Delta^5 + \ldots} \quad (4)$$

$$\Rightarrow U_2^j(\Delta/j)$$

$$= e^{-iH\Delta} + \frac{\Delta^3}{j^2} \widetilde{E}_3(\Delta) + \frac{\Delta^5}{j^4} \widetilde{E}_5(\Delta) + \ldots ,$$

for some error matrices $E_k$ and $\widetilde{E}_k(\Delta)$ that are independent of j. Note that $\widetilde{E}_k(\Delta)$ in the Taylor series has a functional dependence on $\Delta$ due to contributions from $e^{-iH\Delta}$, which has no j dependence.

By taking a linear combination of these unitaries as described in Eq. (1), the cancellation of all lower order error terms may be engineered.

Returning to FIG. 1, at 120, method 100 includes determining, based on the set of exponents $k_j$, the set of pre-factors based on an underdetermined solution to an m×M system of linear equations. For example, the following set of linear equations may be generated for the symmetric Trotter-Suzuki formula:

$$\underbrace{\begin{bmatrix} 1 & 1 & \cdots & 1 \\ k_1^{-2} & k_2^{-2} & \cdots & k_M^{-2} \\ \vdots & \vdots & \ddots & \vdots \\ k_1^{-2m+2} & k_2^{-2m+2} & \cdots & k_M^{-2m+2} \end{bmatrix}}_{V_{m,M}(\vec{k}^{-2})} \underbrace{\begin{bmatrix} a_1 \\ a_2 \\ \vdots \\ a_M \end{bmatrix}}_{\vec{a}} = \underbrace{\begin{bmatrix} 1 \\ 0 \\ \vdots \\ 0 \end{bmatrix}}_{\vec{e}_1} \quad (5)$$

Assuming that the $k_j$ are known a priori, the required cancellations may be cast as this system of linear equations. The left-hand side is a Vandermonde matrix, $V_{m,M}(\vec{k}^{-2}) \in \mathbb{R}^{m \times M}$, where $\vec{k}^{-2} = [k_1^{\{-2\}}, \ldots, k_{\{M\}}^{\{-2\}}]$. In the square case M=m, this has the solution $$a_j = \prod_{q=\{1,\ldots,m\} \setminus j} \frac{k_{[j]}^2}{k_j^2 - k_q^2} = \prod_{q \neq j} \frac{1}{1 - \left(\frac{k_q}{k_j}\right)^2} \quad (6)$$

It may be observed that with the arithmetic progression $k_j = j$, the coefficient $a_m = e^{\Omega(m \log m)}$ is indeed ill-conditioned.

However, a different choice of $k_j$, that is not necessarily an arithmetic progression, may yield coefficients $|a_j|$ that are relatively small. In that case, $U_{\vec{k}}(\Delta)$ may be efficiently applied using standard quantum techniques. To illustrate, one may consider a quantum state preparation circuit $B|0\rangle = |a\rangle = \sum_{j=1}^{m} \sqrt{|a_j|/\|a\|_1} |j\rangle$ and a multiplexer $$S = \sum_{j=1}^{m} |j\rangle\langle j| \otimes (\text{sign}[a_j]U^{k_j}\left(\frac{\Delta}{k_j}\right).$$

These apply the multiproduct formula $(\langle a|_a \otimes I)S(\langle a|_a \otimes I) = U_{\vec{k}}(\Delta)/\|\vec{a}\|_1$ with success probability $1/\|\vec{a}\|_1^2$. Fortunately, that may be amplified using robust oblivious amplitude amplification to $1 - e^{o(m)}(t/\epsilon)^{o(1/m)}(\epsilon)$, so long as $U_{\vec{k}}(\Delta)$ is $\epsilon$-close to being unitary. Each $U_{\vec{k}}(\Delta)$ may be cost in terms of queries made to the underlying product formula $U_2 \cdot S$ queries $U_2 \|\vec{k}\|_1$ times, which then multiplied by $\|\vec{a}\|_1$ for the amplification routine. Clearly, performance is improved with small $\|\vec{a}\|_1$ values.

Returning to FIG. 1, at 130, method 100 includes using the set of exponents $k_j$ and the set of pre-factors $a_j$ to solve the quantum computing problem comprising the product formula.

Values for $k_j$ are real numbers, and typically integers. Previously, values for $k_j$ were selected as arithmetic progressions. Given a progression of $k_j$, values for $a_j$ may be determined using Eq. (5). However, this choice of values leads to coefficients that increase exponentially. Using method 100, any progression of $k_j$ may be selected, and Eq. (5) may be used to derive small coefficients for any given progression.

Well-Conditioned Fractional-Query Multiproduct Formulas

The above-described solution relaxes the conditions of Eq. (1) by allowing the exponents $\vec{k}$ to be arbitrary real numbers. This corresponds to fractional queries to $U_2$, which may be implemented using standard techniques. In this setting, Eq. (5) may be mapped to a polynomial interpolation problem.

For example, consider a set of m polynomials $\{p_j(x) = \sum_{i=1}^{m} A_{j,i} x^{i-1}\}_{j=1}^{m}$ with coefficients represented as the square matrix $A \in \mathbb{R}^{m \times m}$. These may be chosen to be orthogonal over some discrete set of interpolation points $\vec{x}$, that is $\vec{p}_j = [p_j(x_1), p_j(x_2), \ldots, p_j(x_m)]$ and $$\langle \vec{p}_j, \vec{p}_k \rangle = \sum_{i=1}^{m} p_j(x_i) p_k(x_i) \propto \delta_{jk}, \quad (7)$$

where $\delta_{jk}$ is the Kronecker delta function.

Now, the Vandermonde matrix may be left-multiplied by the polynomial coefficients A. Thus, the $j^{th}$ row satisfies $$(A \cdot V_{m,m}(\vec{x}) \cdot \vec{a})_j = \langle \vec{p}_j, \vec{a} \rangle = (A \cdot \vec{e}_1)_j = A_{j,1} \quad (8)$$

Using the orthogonality relationship in Eq. (7), this may be solved by the ansatz $$a_j = f(x_j) = \sum_{i=1}^{m} \frac{A_{i,1} p_i(x_j)}{\langle p_i, p_i \rangle}.$$

The Chebyshev polynomial basis $T_j(x) = \cos(j \cos^{-1}(x))$ thus may furnish a set of multiproduct coefficients with desirable properties.

Lemma 1: Chebyshev Fractional Multiproduct

Choose $V_{m,m}(\vec{x})$ in Eq. (5) with $$x_j = \sin^2\left(\frac{\pi(2j-1)}{4m}\right) \in (0, 1).$$

Then $\vec{a}$ and $\vec{k}$ satisfy $$a_j \in \Theta\left(\frac{1}{j}\right), k_j \in \Theta\left(\frac{m}{j}\right),$$

$\|\vec{a}\|_1 \in \Theta(\log m)$, and $\|\vec{k}\|_1 \in \Theta(m \log m)$.

Proof. Choose a basis set of shifted Chebyshev polynomials $p_j(x) \equiv T_{j-1}(2x-1)$ and interpolate and $$x_j = \sin^2\left(\frac{\pi(2j-1)}{4m}\right).$$

For example, the Chebyshev polynomials facts $$\langle p_j, p_k \rangle = \frac{m}{2} \delta_{jk}(1 + \delta_{j1})$$

and $p_j(0) = -(-1)^j$ may be used.

Thus the function $$f\left(\frac{1+\cos\theta}{2}\right) = \sum_{j=0}^{m-1} \frac{(-1)^j \cos(j\theta)}{\frac{m}{2}(1+\delta_{j0})},$$

implies $a_j =$ $$f(x_j) = \frac{(-1)^{j+1}}{m}\cot\left(\frac{\pi(2j-1)}{4m}\right),$$

$$\|\vec{a}\|_1 \le \sum_{j=1}^{m} \frac{2}{2j-1} \le \log(e^2(2m-1)) \in O(\log(m)), \quad (9)$$

$$\|\vec{k}\|_1 \le \sum_{j=1}^{m} \frac{2m}{2j-1} \in O(m\log m),$$

where the fact $k_j = 1/\sqrt{x_j}$ and the inequality $\forall x \in [0, \pi/2]$, $$\cot(x) \le \frac{\pi}{2x}$$

have been used.

This solution is remarkably robust to perturbations. For instance, dropping the latter half of $x_j$ does not affect its qualitative properties, as seen in the following result.

Lemma 2: Half-Chebyshev Fractional Multiproduct

Choose $V_{m,m}(\vec{x})$ in Eq. (5) with $$x_j = \sin^2\left(\frac{\pi(2j-1)}{8m}\right) \in (0, 1/2).$$

Then $\vec{a}$ and $\vec{k}$ scale as in Lemma 1.

Proof. Bootstrap off the solution in Lemma 1 with 2m interpolation points $$\left\{\tilde{x}_j = \sin^2\left(\frac{\pi(2j-1)}{8m}\right)\right\}_{j=1}^{2m}$$

which has multiproduct coefficients $\{\tilde{a}_j\}_{j=1}^{2m}$ given by Eq. (9). Using the exact solution Eq. (6), it may be observed that $$\forall j \in [1, m], \tilde{a}_J = a_j \prod_{q=m+1}^{2n} \frac{1}{1 - \tilde{x}_j/\tilde{x}_q} \ge a_j, \quad (10)$$

which follows from $0 < \tilde{x}_j < \tilde{x}_q$ for all $1 \le j < q \le 2m$. Similarly to Lemma 1, the quantities $$a_j \le \frac{2}{2j-1} \Rightarrow \|\vec{a}\|_1 \le \log(e^2(2m-1)),$$

and $$k_j \le \frac{2\sqrt{2}\,m}{2j-1} \Rightarrow \|\vec{k}\|_1 \in O(m\log m)$$

may be evaluated.

Well-Conditioned Integer-Query Multiproduct Formulas

Lemmas 1 and 2 choose $k_j$ to be real numbers but not necessarily integers. This shows, generally, that with real numbers Eq. (5) can be solved to get very small coefficients. Since both sums of exponents and coefficients are small, their product is small, and so higher order product formulas can be used at reduced cost. However, solutions that use real numbers for $k_j$ may be impractical to implement. Still, this provides proof-of the-principle that, if you can use real numbers for $k_j$, cost can be reduced.

It may now be shown that the fractional query solutions may be converted into integer query solutions by rescaling with a suitable constant K and rounding each exponent $k_j = K/\sqrt{x_j}$, to a different integer $l_j$—otherwise $V(\vec{1}^{-2})$ becomes singular. This bootstrapping doesn't raise the cost significantly and may still yield polynomial scaling of the coefficients with respect to the order.

Rounding also perturbs the multiproduct coefficients d, but similar to the robustness of Lemma 2, $\|\vec{a}\|_1$ changes by at most a multiplicative constant, as shown below.

Lemma 3: Half-Chebyshev Integer Multiproduct

Choose $V_{m,m}(\vec{1}^{-2})$ in Eq. (5), where $l_j = \lceil k_j \rceil$, $k_j = K/\sqrt{x_j}$, $x_j$ are from Lemma 2, and $K \in \Theta(m)$. Then $\|\vec{a}\|_1 \in \Theta(\log m)$, and $\|\vec{l}\|_1 \in \Theta(m^2 \log m)$.

Proof From the definition of $x_j$, note that $k_j \in \Theta(Km/j)$, and $K \in \Theta(m)$ in order for $l_j$ and $k_j$ to round to unique integers. Thus the perturbation $|l_j - k_j| = \delta_j \in \Theta(K/m)$ and the fractional change in $\gamma_q = (k_q/k_j)^2$ is $$\frac{l_q^2}{l_j^2} = \frac{k_q^2}{k_j^2}(1 + \Delta[q, j]), |\Delta[q, j]| \in \Theta\left(\frac{|q-j|}{m^2}\right), \quad (11)$$

where the sign of $\Delta[q, j]$ matches the sign of $(q-j)$.

The change between $$a_j = \prod_{q \ne j} \frac{1}{1 - (l_q/l_j)^2}$$

and the original $$\tilde{a}_J = \prod_{q \ne j} \frac{1}{1 - (k_q/k_j)^2}$$

may now be evaluated. As $\Delta[q, j]$ is small, the shift in $\tilde{a}_j$ to leading order may be evaluated by using the derivatives $$\frac{\partial \tilde{a}_J}{\partial \gamma_q} = \frac{\tilde{a}_J}{1 - \gamma_q}.$$

Thus $$\frac{|a_j - \widetilde{x_l}|}{|\widetilde{a_j}|} \in \Theta\left(\sum_{q \neq j} \frac{\Delta[q,j]}{1-\gamma_q}\right) \in \quad (12)$$

$$\Theta\left(\sum_{q \neq j} \frac{x_q|q-j|}{m^2|x_q - x_j|}\right) \in \Theta\left(\sum_{q \neq j} \frac{q^2|q-j|}{m^2|q-j|(q+j)}\right) \in \Theta(1),$$

where in the last line, asymptotic expressions are substituted for $x_j$, $x_q$.

As the exponents $k_j$ have been chosen a priori, a smaller one-norm $\|\vec{a}\|_1$ might be possible if $\|\vec{a}\|_1$ is minimized over to all $$\binom{M}{m}$$

subsets $\{k_j\}_{j=1}^m \subseteq [M]$. Surprisingly, exact solutions to this discrete optimization problem can be obtained efficiently through the linear program $$\min_{\vec{a}} \|\vec{a}\|_1 \text{ s.t. } V_{m,M}(\vec{k}^{-2}) \cdot \vec{a} = \vec{e}_1 \text{ and } k_j = j, \quad (13)$$

followed by minimizing with respect to $m \in [M]$. Importantly, minimizing the one-norm also ensures that the solution d has exactly m non-zero elements, analogous to sparse signal recovery in compressed sensing. In this context, "minimizing" refers to a procedure for reducing the relative values and/or sums of components, and not necessarily to deriving a global minimum value.

Eq. (5) has traditionally be chosen to be a square matrix, meaning that the number of free parameters (k) is exactly equal to the order of the integrator. Herein, Eq. (5) is being solved as an underdetermined system, meaning that there are excess free parameters. In other words, there can be more values for $k_j$ than the order M of the integrator. By solving this underdetermined system, using the phrasing of the optimization problem in Eq. (13), solutions can be derived that are sparse. As one example, sparse solutions include as many $a_j$ values as possible will be =0. Additionally or alternatively, a subset of $a_j$ values are set to zero and/or small values. As such, even though there is an arithmetic progression in Vandermonde matrix in Eq. (5), in some examples all of the coefficients that can be zero are set to zero, assuming that the one-norm of these coefficients is as small as possible. By making the solution sparse, the cost of the algorithm also depends on one-norm of $k_j$, but if the coefficient of $a_j$ is 0, the corresponding $k_j$ is not applied, and the one-norm of k is only a sum of the $k_j$ values that are associated with a positive $a_j$ value.

Worst-Case Error Bounds

Rigorous, but loose, bounds may now be provided on the error of multiproduct integrators, thus completing the proof of Theorem 1.

Proof of Theorem 1. Denote the remainder of any function by $\mathcal{R}_m[\Sigma_{j=0}^\infty c_j x^j] = \Sigma_{j=m+1}^\infty c_j x^j$. Observe the remainder of the product formula $$\|\mathcal{R}_m[U_2^j(\Delta/j) - e^{-iH\Delta}]\| \leq 2\frac{|\Delta\lambda|^{m+1}}{(m+1)!} e^{|\Delta\lambda|} \quad (14)$$

has an error bound independent of the exponent j, where $\lambda = \Sigma_{j=1}^N \|h_j\|$, and the inequalities $$|\mathcal{R}_m[e^\lambda]| \leq \frac{|\lambda|^{m+1}}{(m+1)!} e^{|\lambda|}$$

and $\|\mathcal{R}_m[\Pi_j e^{\Delta h_j}]\| \leq \|\mathcal{R}_m[e^{\Sigma_j|\Delta|\|h_j\|}]\|$ have been used.

Thus, a single multiproduct segment has error $$\|U_{\vec{k}}(\Delta) - e^{-iH\Delta}\| \leq 2\|\vec{a}\|_1 \frac{|\Delta\lambda|^{2m+2}}{(2m+2)!} e^{|\Delta\lambda|} = \epsilon_\Delta. \quad (15)$$

By applying $r \leq 1/\epsilon_{t/r}$ segments and using the inequality $(1+\epsilon_{t/r})^r \leq e^{r\epsilon_{t/r}} \leq 1+2r\epsilon_{t/r}$, the error of longer time t simulations is $$\epsilon = \|U_{\vec{k}}^r(t/r) - e^{-iHt}\| \leq 4r\|\vec{a}\|_1 \frac{|t\lambda/r|^{2m+2}}{(2m+2)!} e^{|t\lambda/r|}.$$

Choose, for example, $$r = t\lambda \left(\frac{8t\lambda \|\vec{a}\|_1}{\epsilon(2m+2)!}\right)^{1/(2m+1)} \geq t\lambda/\log 2.$$

Now define $z = W(\log(t\lambda/\epsilon))$ using the Lambert-W function which solves $\log(t\lambda/\epsilon) = (z)e^z$, and choose $2m+1 = e^z$. The number of exponentials required in total to implement $U_{\vec{k}}^r(t/r)$ is then $$r\|\vec{a}\|_1\|\vec{k}\|_1 = t\lambda e^{\frac{\log(t\lambda/\epsilon)}{2m+1} + \log m + O(\log\log m)} = \quad (16)$$

$$t\lambda e^{\frac{\log(t\lambda/\epsilon)}{e^z} + z + O(\log z)} = t\lambda e^{2z + O(\log z)} \in O(t\lambda \log^{2+o(1)}(t\lambda/\epsilon)),$$

where $\|\vec{a}\|_1\|\vec{k}\|_1$ scale according to Lemma 3.

Figure 2:
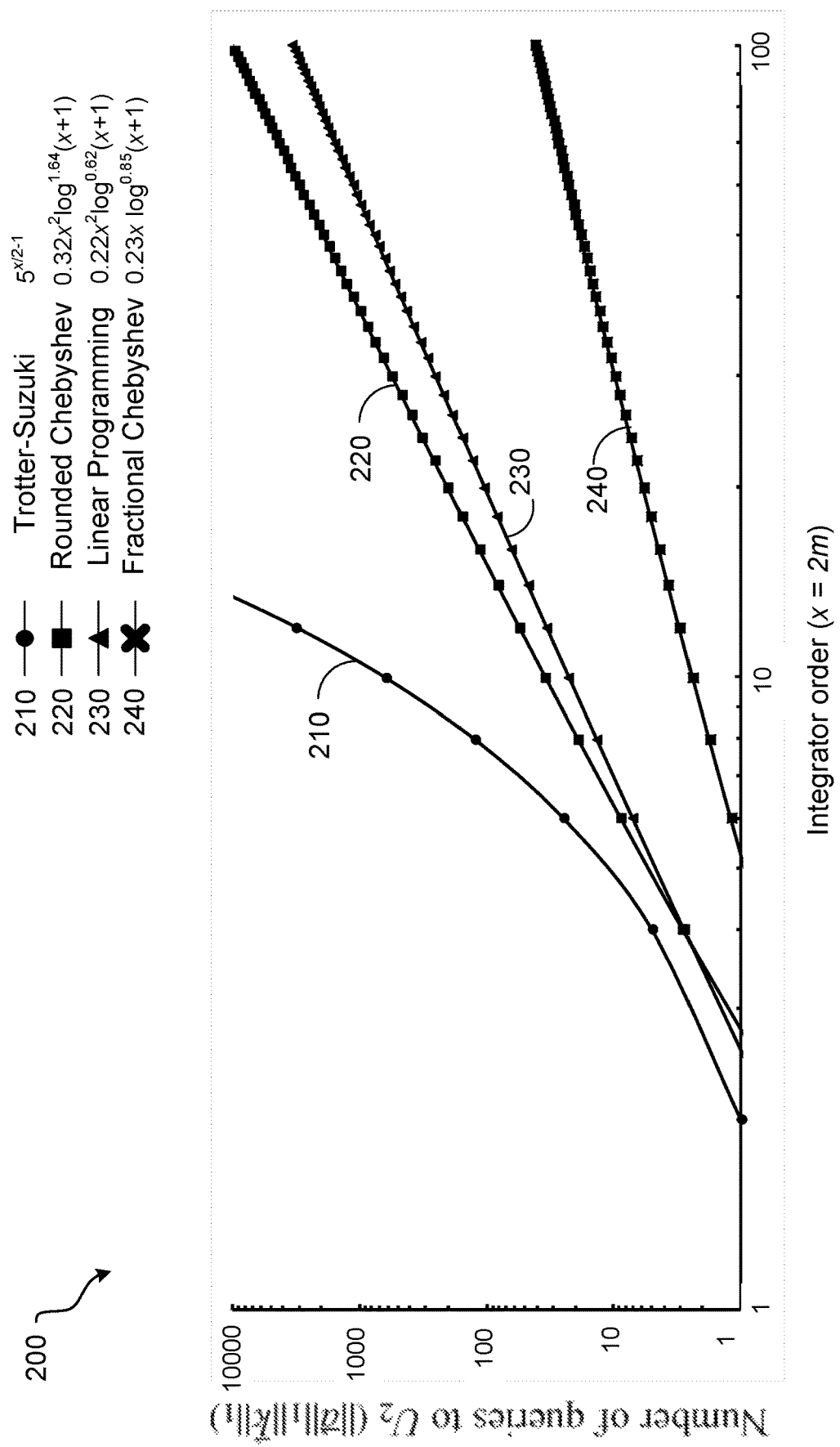
FIG. 2 shows a graph plotting a number of queries against an integrator order using either classic product formulas or variations of the method of FIG. 1.

FIG. 2 shows a graph 200 comparing the relative costs of the classic Trotter-Suzuki product formula and different implementations of the methods described herein. Graph 200 plots the number of queries to the second-order Trotter-Suzuki formula $U_2$ made for each step of an order 2m integrator. Plot 210 represents the Trotter-Suzuki formula. Plot 220 represents the rounded Chebyshev approach of Lemma 3. Plot 230 represents linear programming. Plot 240 represents the fractional Chebyshev approach of Lemma 1. As predicted, the fractional query solution of plot 240 has a very small cost but may be more complex to implement. The rounded Chebyshev solution of plot 220 results from bootstrapping off of the fractional query solution. While not quite as low cost as the linear programming of plot 230, this rounded Chebyshev solution represents a significant cost reduction when compared to Trotter-Suzuki. For very small systems—e.g. 15 qubits—minimizing the cost allows the use of integrators approaching 10th order. As computing systems increase in size, the order of the integrator can increase accordingly.

These theoretical solutions scale similarly to the minimized solutions (e.g. the solutions that are the result of the minimization process, which may or may not be actual minima), which are presented in Table 1. Table 1 presents multi-product solutions to Eq. (1) that minimize $\|\vec{a}\|_1 \|\vec{k}\|_1$, where $\vec{k}$ only contains the $k_j$ exponents that correspond to non-zero $a_j$ coefficients. Both theoretical and practical solutions allow for the generation and application of higher order, yet low-cost product formulas as applied to solving quantum computing application, such as the time-evolution of a Hamiltonian. The technical effects of implementing these solutions include a reduction in the number of computing operations needed to generate a solution, reducing the time and computing power necessary to perform quantum simulations.

TABLE 1

Non-zero coefficients of optimized multi-product formulas $$U_{\vec{k}}(\Delta) = \sum_{j=1}^{M} a_j U_2^{k_j}\left(\frac{\Delta}{k_j}\right) = e^{-iH\Delta} + O((N|h|\Delta)^{2m+2})$$

| m | $\|\vec{a}\|_1$ | $\|\vec{k}\|_1$ | |
|---|---|---|---|
| 2 | 1.667 | 3 | $a_1 = -\frac{1}{3}, a_2 = \frac{4}{3}$ |
| 3 | 1.333 | 9 | $a_1 = \frac{1}{105}, a_2 = -\frac{1}{6}, a_6 = \frac{81}{70}$ |
| 4 | 1.401 | 16 | $a_1 = -\frac{1}{2376}, a_2 = \frac{2}{45}, a_3 = -\frac{729}{3640}, a_{10} = \frac{31250}{27027}$ |
| 5 | 1.373 | 28 | $a_1 = \frac{1}{165888}, a_2 = -\frac{256}{89775}, a_3 = \frac{6561}{179200}, a_5 = -\frac{390625}{2128896},$ $a_{17} = \frac{6975757441}{6067353600}$ |
| 6 | 1.530 | 37 | $a_1 = -\frac{1}{5544000}, a_2 = \frac{8}{19665}, a_3 = -\frac{81}{4480}, a_4 = \frac{65536}{669375}, a_6 = -\frac{216}{875},$ $a_{21} = \frac{7626831723}{6537520000}$ |
| 7 | 1.365 | 58 | $a_1 = \frac{1}{798336000}, a_2 = -\frac{8}{654885}, a_3 = \frac{59049}{41108480}, a_4 = -\frac{1048576}{52518375},$ $a_5 = \frac{244140625}{4596673536}, a_9 = -\frac{31381059609}{192832640000}, a_{34} = \frac{4660977897838088}{4131462743533125}$ |
| 8 | 13.72 | 78 | $a_1 = -\frac{1}{87524236800}, a_2 = \frac{32}{66844575}, a_3 = -\frac{729}{5017600}, a_4 = \frac{131072}{28477575},$ $a_5 = -\frac{48828125}{1520031744}, a_6 = \frac{23328}{425425}, a_{12} = -\frac{95551488}{622396775},$ $a_{45} = \frac{15322783012207031 25}{13603896503332495 36}$ |
| 9 | 1.357 | 102 | $a_1 = \frac{1}{14351497574400}, a_2 = -\frac{4}{328930875}, a_3 = \frac{59049}{6613376000},$ $a_4 = -\frac{4194304}{7439025825}, a_5 = \frac{6103515625}{831680898048}, a_6 = -\frac{59049}{2452450},$ $a_8 = \frac{274877906944}{5654031508125}, a_{15} = -\frac{360406494140625}{2342511781722112},$ $a_{58} = \frac{25024647368034734878 7521}{22293034090980463936 1250}$ |
| 10 | 1.359 | 128 | $a_1 = -\frac{1}{2405702668723200}, a_2 = \frac{1}{3304192500}, a_3 = -\frac{177147}{328182400000},$ $a_4 = \frac{16777216}{244314672525}, a_5 = -\frac{152587890625}{88665552847872}, a_6 = \frac{177147}{14314300},$ $a_7 = -\frac{1628413597910449}{64065702729600000}, a_{10} = \frac{152587890625}{3090381882588},$ |

TABLE 1-continued

Non-zero coefficients of optimized multi-product formulas $$U_{\vec{k}}(\Delta) = \sum_{j=1}^{M} a_j U_2^{k_j}\left(\frac{\Delta}{k_j}\right) = e^{-iH\Delta} + \mathcal{O}((N|h|\Delta)^{2m+2})$$

| m | $\|\vec{a}\|_1$ | $\|\vec{k}\|_1$ | |
|---|---|---|---|
| | | | $a_{18} = -\dfrac{7625597484987}{50102940387500}, a_{72} = \dfrac{3353773241393051236879564 8}{300108925864415601589906 25}$ |
| 11 | 1.358 | 158 | $a_1 = \dfrac{1}{489053083097779200}, a_2 = -\dfrac{4}{648001265625}$, |
| | | | $a_3 = \dfrac{4782969}{181060880000000}, a_4 = -\dfrac{524288}{79303299075}$, |
| | | | $a_5 = \dfrac{95367431640625}{3150520067950295 04}, a_6 = -\dfrac{9565938}{2362935575}$, |
| | | | $a_7 = \dfrac{79792266297612001}{4243214845584000000}, a_8 = -\dfrac{137438953472}{5028288890625}$, |
| | | | $a_{12} = \dfrac{2507653251072}{57111976796875}, a_{22} = -\dfrac{11119834626984462962}{75338562178830234375}$, |
| | | | $a_{88} = \dfrac{7641492169572260403506126520 32}{6847391902138408378730060156 25}$ |
| 12 | 1.350 | 193 | $a_1 = -\dfrac{1}{1443902391425894400 00}, a_2 = \dfrac{1}{11687273325000}$, |
| | | | $a_3 = -\dfrac{129140163}{1506389928243200 00}, a_4 = \dfrac{1073741824}{2652237835025625}$, |
| | | | $a_5 = -\dfrac{95367431640625}{3025491514793459712}, a_6 = \dfrac{129140163}{188838650000}$, |
| | | | $a_7 = -\dfrac{79792266297612001}{15530574349255680000}, a_8 = \dfrac{4503599627370496}{352223792657611875}$, |
| | | | $a_{10} = -\dfrac{95367431640625}{4105747222248672}, a_{14} = \dfrac{79792266297612001}{1838945428407945000}$, |
| | | | $a_{27} = -\dfrac{3815204244769458316286498 98809}{2599557522032734399084748 800000}$ |
| | | | $a_{106} = \dfrac{8591502705999260761126830381 0877410409}{7682645867032782709970073967 5297300000}$ |
| 13 | 1.376 | 224 | $a_1 = \dfrac{1}{31462070283141120 000000}, a_2 = -\dfrac{8192}{5071269939762151125}$, |
| | | | $a_3 = \dfrac{1162261467}{30384094532599808000}, a_4 = -\dfrac{68719476736}{1985545575685546875}$, |
| | | | $a_5 = \dfrac{59604644775390625}{126951309642244565 23776}, a_6 = -\dfrac{9521245937664}{55318072575390625}$, |
| | | | $a_7 = \dfrac{191581231380566414401}{8469075703301878579 2000}, a_8 = -\dfrac{288230376151711744}{24270307981988693625}$, |
| | | | $a_9 = \dfrac{984770902183611232881}{4376058045399040000000 0}, a_{11} = -\dfrac{81402749386839761113321}{30097209570243379200000 00}$, |
| | | | $a_{16} = \dfrac{48357032784585166988247 04}{112513856873765905761328 125}$ |
| | | | $a_{31} = -\dfrac{620412660965527688188300 451573157121}{417343797193076417542965 1660800000000}$ |

TABLE 1-continued

Non-zero coefficients of optimized multi-product formulas $$U_{\vec{k}}(\Delta) = \sum_{j=1}^{M} a_j U_2^{k_j}\left(\frac{\Delta}{k_j}\right) = e^{-iH\Delta} + \mathcal{O}((N|h|\Delta)^{2m+2})$$

| m | $\|\vec{a}\|_1$ | $\|\vec{k}\|_1$ | |
|---|---|---|---|
| | | | $a_{121} = \dfrac{8017953205361335735719315346653802331738415339 61}{715886828276024991553383459008280526848000000000}$ |
| 14 | 1.343 | 271 | $a_1 = -\dfrac{1}{12947955743587345367040000},\ a_2 = \dfrac{4096}{25596857080777795312 5},$ |
| | | | $a_3 = -\dfrac{387420489}{439666742394880000000},\ a_4 = \dfrac{4398046511104}{2954011765908438860625},$ |
| | | | $a_5 = -\dfrac{59604644775390625}{176199152307255474388992},\ a_6 = \dfrac{793437161472}{40323113771565625},$ |
| | | | $a_7 = -\dfrac{1915812313805664144 01}{473539419700199424000000},\ a_8 = \dfrac{295147905179352825856}{856571949189529541718 75},$ |
| | | | $a_9 = -\dfrac{8862938119652501095929}{70374015062889201664 0000},\ a_{10} = \dfrac{122070312500000000000}{7299214348532926488669},$ |
| | | | $a_{13} = -\dfrac{9173333019326861665839961 6009}{49116604553208567064166400000 00},$ |
| | | | $a_{19} = \dfrac{17684534180768657011955825953294 81}{4746183381296366832761501122560000 0},$ |
| | | | $a_{37} = -\dfrac{59325966985223687799599734398071581327609}{42432545558678332612354003703955456000000 0},$ |
| | | | $a_{147} = \dfrac{696762206271866268428168706860580089445450671440761}{6254382555717644276228669818265124841896017920000000 0}$ |
| 15 | 1.340 | 316 | $a_1 = \dfrac{1}{57089346161404166412042240 00},\ a_2 = -\dfrac{1}{6792655122878625000},$ |
| | | | $a_3 = \dfrac{4782969}{256012756679680000000},\ a_4 = -\dfrac{8589934592}{147809328285209716125},$ |
| | | | $a_5 = \dfrac{476837158203125}{22035963278560349454336},\ a_6 = -\dfrac{4782969}{2477563088000},$ |
| | | | $a_7 = \dfrac{1341068619663964900807}{228481002166239313920000 00},\ a_8 = -\dfrac{18446744073709551616}{25299400178786092734375},$ |
| | | | $a_9 = \dfrac{8862938119652501095929}{2254956509146578485248000},\ a_{10} = -\dfrac{476837158203125}{58708966584812544},$ |
| | | | $a_{12} = \dfrac{4565043429507072}{3327842746509531 25},\ a_{15} = -\dfrac{253410816192626953125}{11861507876217629966336},$ |
| | | | $a_{22} = \dfrac{14420993610649923403767606408 1}{3575238879657630656278080000 000},$ |
| | | | $a_{42} = -\dfrac{7126988483028371708497728 87}{51028487217430786835200000 00},$ |
| | | | $a_{170} = \dfrac{1351885436862359089266305321028854417800903320 3125}{1215897631925226017561199933193826128270429935206 4}$ |

Although primarily described with regard to symmetric product formulas, such as the second order symmetric Trotter-Suzuki product formula, similar methods may be applied to other product formula types. For example, variations on the expansion shown in Eq. (4) may yield variations on the Vandermonde matrix shown in Eq (5). Solutions to these variations may be used to generate valid multiproduct formulas.

For example, when the underlying product formula is symmetric and of order α, rather than order 2, a slightly different system of equations may be solved:

$$\underbrace{\begin{bmatrix} 1 & 1 & \cdots & 1 \\ k_1^{-\alpha} & k_2^{-\alpha} & \cdots & k_M^{-\alpha} \\ k_1^{-\alpha-2} & k_2^{-\alpha}-2 & \cdots & k_M^{-\alpha-2} \\ \vdots & \vdots & \ddots & \vdots \\ k_1^{-2m+2} & k_2^{-2m+2} & \cdots & k_M^{-2m+2} \end{bmatrix}}_{V_{m,M}(\vec{k}^{-\alpha})} \underbrace{\begin{bmatrix} a_1 \\ a_2 \\ a_3 \\ \vdots \\ a_M \end{bmatrix}}_{\vec{a}} = \underbrace{\begin{bmatrix} 1 \\ 0 \\ 0 \\ \vdots \\ 0 \end{bmatrix}}_{\vec{e}_1} \quad (17)$$

When the underlying product formula is non-symmetric and of order 1, the following system of equations may be solved:

$$\underbrace{\begin{bmatrix} 1 & 1 & \cdots & 1 \\ k_1^{-1} & k_2^{-1} & \cdots & k_M^{-1} \\ \vdots & \vdots & \ddots & \vdots \\ k_1^{-m+1} & k_2^{-m+1} & \cdots & k_M^{-m+1} \end{bmatrix}}_{V_{m,M}(\vec{k}^{-1})} \underbrace{\begin{bmatrix} a_1 \\ a_2 \\ \vdots \\ a_M \end{bmatrix}}_{\vec{a}} = \underbrace{\begin{bmatrix} 1 \\ 0 \\ \vdots \\ 0 \end{bmatrix}}_{\vec{e}_1} \quad (18)$$

When the underlying product formula is non-symmetric and of order α, the following system of equations may be solved:

$$\underbrace{\begin{bmatrix} 1 & 1 & \cdots & 1 \\ k_1^{-\alpha} & k_2^{-\alpha} & \cdots & k_M^{-\alpha} \\ k_1^{-\alpha-1} & k_2^{-\alpha-1} & \cdots & k_M^{-\alpha-1} \\ \vdots & \vdots & \ddots & \vdots \\ k_1^{-m+1} & k_2^{-m+1} & \cdots & k_M^{-m+1} \end{bmatrix}}_{V_{m,M}(\vec{k}^{-\alpha})} \underbrace{\begin{bmatrix} a_1 \\ a_2 \\ a_3 \\ \vdots \\ a_M \end{bmatrix}}_{\vec{a}} = \underbrace{\begin{bmatrix} 1 \\ 0 \\ 0 \\ \vdots \\ 0 \end{bmatrix}}_{\vec{e}_1} \quad (19)$$

As described for Eq. (5), underdetermined solutions to Eqs. (17-19) may be generated such that $k_j$ is not necessarily an arithmetic progression, (e.g., using Eq. (13)). By being more flexible in choosing the exponents $k_j$, well-conditioned multiproduct formulas may be generated with desirable properties, wherein the sum of absolute values of the coefficients is relatively small.

In some embodiments, the methods and processes described herein may be tied to a quantum computing system of one or more quantum computing devices. FIG. 4 shows aspects of an example quantum computer 310 configured to execute quantum-logic operations (vide infra). Whereas conventional computer memory holds digital data in an array of bits and enacts bit-wise logical operations, a quantum computer holds data in an array of qubits and operates quantum-mechanically on the qubits in order to implement the desired logic. Accordingly, quantum computer 310 of FIG. 3 includes at least one register 312 comprising an array of qubits 314. The illustrated register is eight qubits in length; registers comprising longer and shorter qubit arrays are also envisaged, as are quantum computers comprising two or more registers of any length.

The qubits of register 312 may take various forms, depending on the desired architecture of quantum computer 310. Each qubit 314 may comprise: a superconducting Josephson junction, a trapped ion, a trapped atom coupled to a high-finesse cavity, an atom or molecule confined within a fullerene, an ion or neutral dopant atom confined within a host lattice, a quantum dot exhibiting discrete spatial- or spin-electronic states, electron holes in semiconductor junctions entrained via an electrostatic trap, a coupled quantum-wire pair, an atomic nucleus addressable by magnetic resonance, a free electron in helium, a molecular magnet, or a metal-like carbon nanosphere, as nonlimiting examples. More generally, each qubit 314 may comprise any particle or system of particles that can exist in two or more discrete quantum states that can be measured and manipulated experimentally. For instance, a qubit may also be implemented in the plural processing states corresponding to different modes of light propagation through linear optical elements (e.g., mirrors, beam splitters and phase shifters), as well as in states accumulated within a Bose-Einstein condensate.

FIG. 4 is an illustration of a Bloch sphere 316, which provides a graphical description of some quantum mechanical aspects of an individual qubit 314. In this description, the north and south poles of the Bloch sphere correspond to the standard basis vectors |0> and |1>, respectively—up and down spin states, for example, of an electron or other fermion. The set of points on the surface of the Bloch sphere comprise all possible pure states |Ψ> of the qubit, while the interior points correspond to all possible mixed states. A mixed state of a given qubit may result from decoherence which may occur because of undesirable couplings to external degrees of freedom.

Returning now to FIG. 3, quantum computer 310 includes a controller 318. The controller may comprise conventional electronic componentry, including at least one processor 320 and associated storage machine 322. The term 'conventional' is applied herein to any component that can be modeled as an ensemble of particles without considering the quantum state of any individual particle. Conventional electronic components include integrated, microlithographed transistors, resistors, and capacitors, for example. Storage machine 322 may be configured to hold program instructions 324 that cause processor 320 to execute any process described herein. Additional aspects of controller 318 are described hereinafter.

Controller 318 of quantum computer 310 is configured to receive a plurality of inputs 326 and to provide a plurality of outputs 328. The inputs and outputs may each comprise digital and/or analog lines. At least some of the inputs and outputs may be data lines through which data is provided to and extracted from the quantum computer. Other inputs may comprise control lines via which the operation of the quantum computer may be adjusted or otherwise controlled.

Controller 318 is operatively coupled to register 312 via interface 330. The interface is configured to exchange data billirectionally with the controller. The interface is further configured to exchange signal corresponding to the data billirectionally with the register. Depending on the architecture of quantum computer 310, such signal may include electrical, magnetic, and/or optical signal. Via signal conveyed through the interface, the controller may interrogate and otherwise influence the quantum state held in the register, as defined by the collective quantum state of the array of qubits 314. To this end, the interface includes at least one modulator 332 and at least one demodulator 334, each coupled operatively to one or more qubits of register 312. Each modulator is configured to output a signal to the register based on modulation data received from the controller. Each demodulator is configured to sense a signal from the register and to output data to the controller based on the signal. The data received from the demodulator may, in some scenarios, be an estimate of an observable to the measurement of the quantum state held in the register.

More specifically, suitably configured signal from modulator 332 may interact physically with one or more qubits 314 of register 312 to trigger measurement of the quantum state held in one or more qubits. Demodulator 334 may then sense a resulting signal released by the one or more qubits pursuant to the measurement, and may furnish the data corresponding to the resulting signal to the controller. Stated another way, the demodulator may be configured to reveal, based on the signal received, an estimate of an observables reflecting the quantum state of one or more qubits of the register, and to furnish the estimate to controller 318. In one non-limiting example, the modulator may provide, based on data from the controller, an appropriate voltage pulse or pulse train to an electrode of one or more qubits, to initiate a measurement. In short order, the demodulator may sense photon emission from the one or more qubits and may assert a corresponding digital voltage level on an interface line into the controller. Generally speaking, any measurement of a quantum-mechanical state is defined by the operator $\hat{O}$ corresponding to the observable to be measured; the result R of the measurement is guaranteed to be one of the allowed eigenvalues of $\hat{O}$. In quantum computer 310, R is statistically related to the register state prior to the measurement, but is not uniquely determined by the register state.

Pursuant to appropriate input from controller 318, interface 330 may be further configured to implement one or more quantum-logic gates to operate on the quantum state held in register 312. Whereas the function of each type of logic gate of a conventional computer system is described according to a corresponding truth table, the function of each type of quantum gate is described by a corresponding operator matrix. The operator matrix operates on (i.e., multiplies) the complex vector representing the register state and effects a specified rotation of that vector in Hilbert space.

Figure 3:
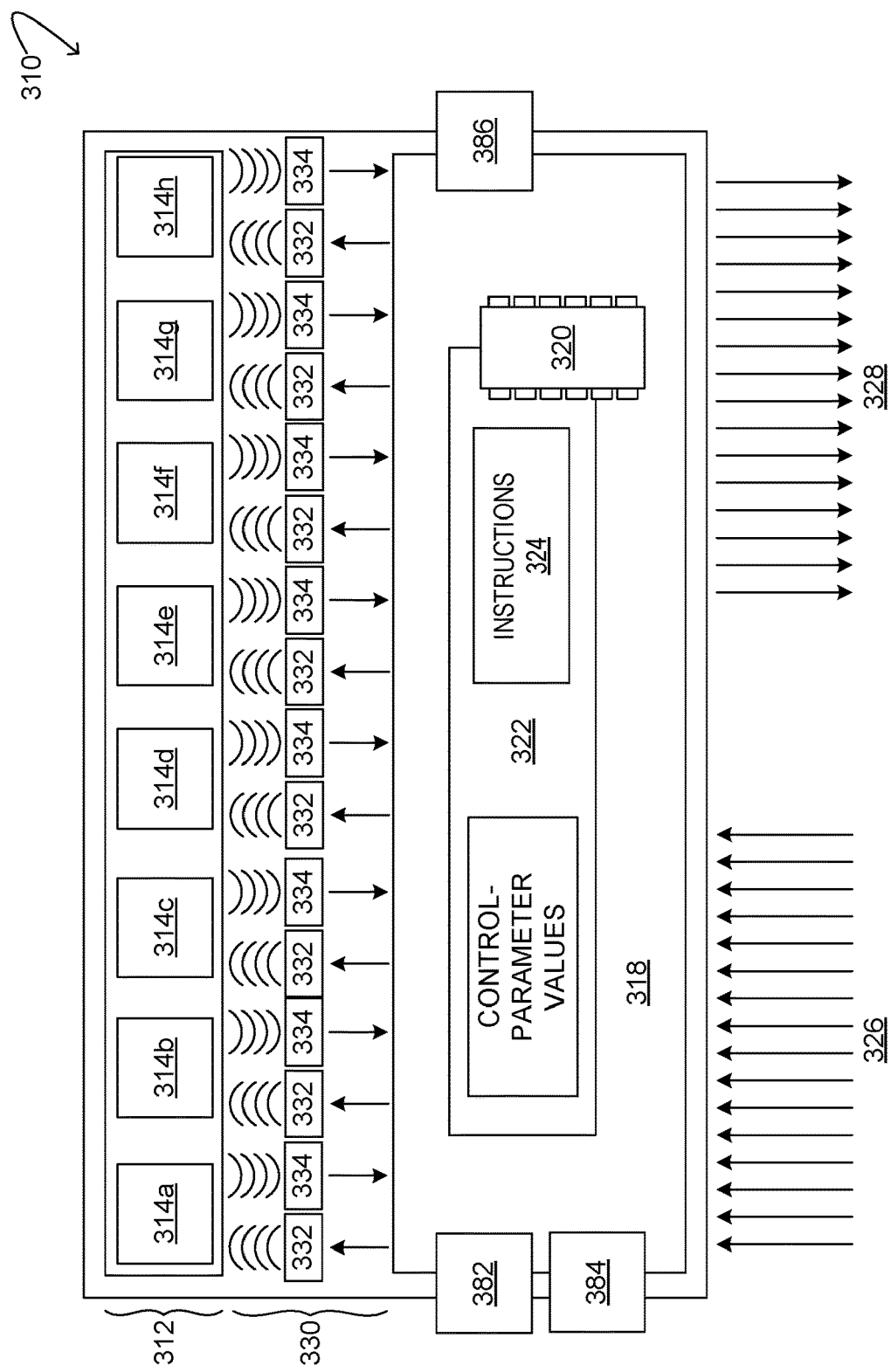
FIG. 3 schematically shows aspects of an example quantum computer.
Figure 4:
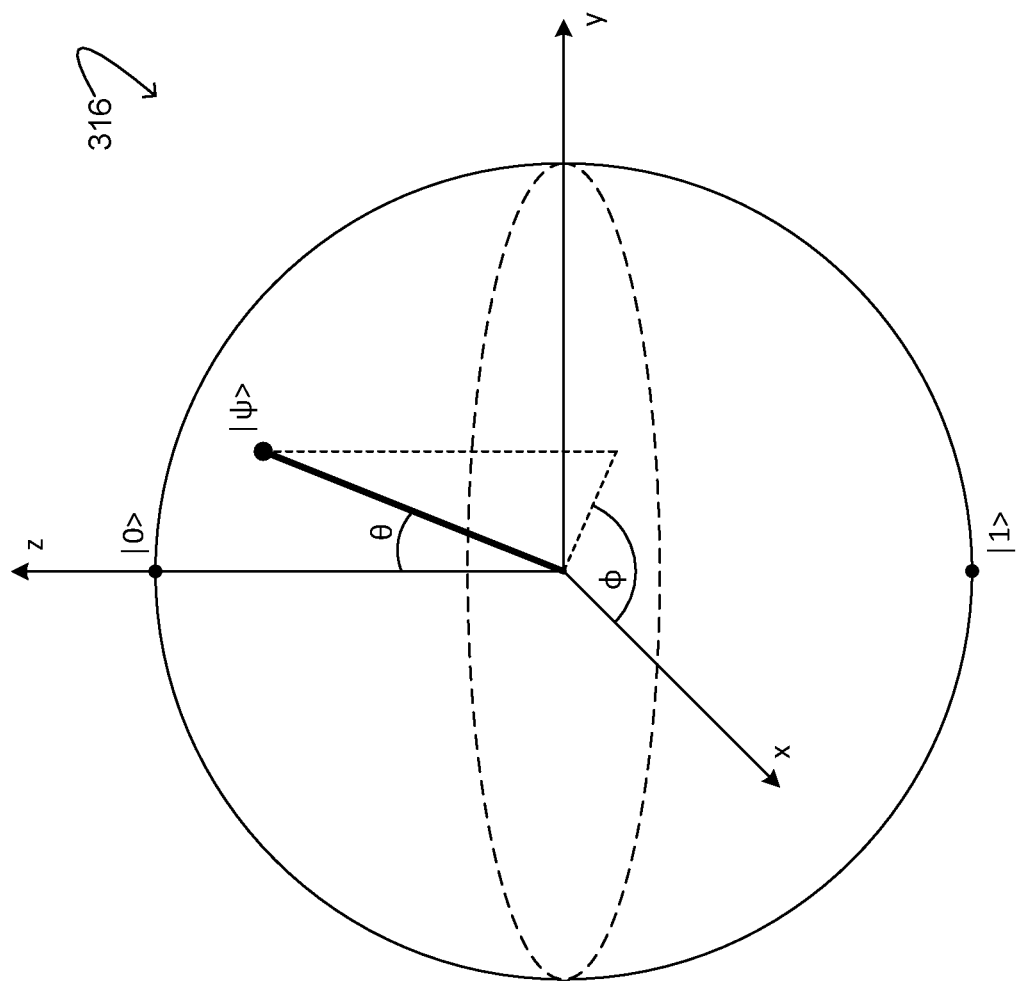
FIG. 4 illustrates a Bloch sphere, which graphically represents the quantum state of one qubit of a quantum computer.

Continuing in FIG. 3, suitably configured signal from modulators 332 of interface 330 may interact physically with one or more qubits 314 of register 312 so as to assert any desired quantum-gate operation. As noted above, the desired quantum-gate operations are specifically defined rotations of a complex vector representing the register state. In order to effect a desired rotation $\hat{O}$, one or more modulators of interface 330 may apply a predetermined signal level $S_i$ for a predetermined duration $T_i$.

In some examples, plural signal levels may be applied for plural sequences or otherwise associated durations. In a more particular example, the plural signal levels and durations are arranged to form a composite signal waveform, which may be applied to one or more qubits of the register. In general, each signal level $S_i$ and each duration $T_i$ is a control parameter adjustable by appropriate programming of controller 318. In other quantum-computing architectures, different sets of adjustable control parameters may control the quantum operation applied to the register state.

In some embodiments, the methods and processes described herein may be tied to a classical computing system of one or more classical computing devices. In particular, such methods and processes may be implemented as a computer-application program or service, an application-programming interface (API), a library, and/or other computer-program product.

Figure 5:
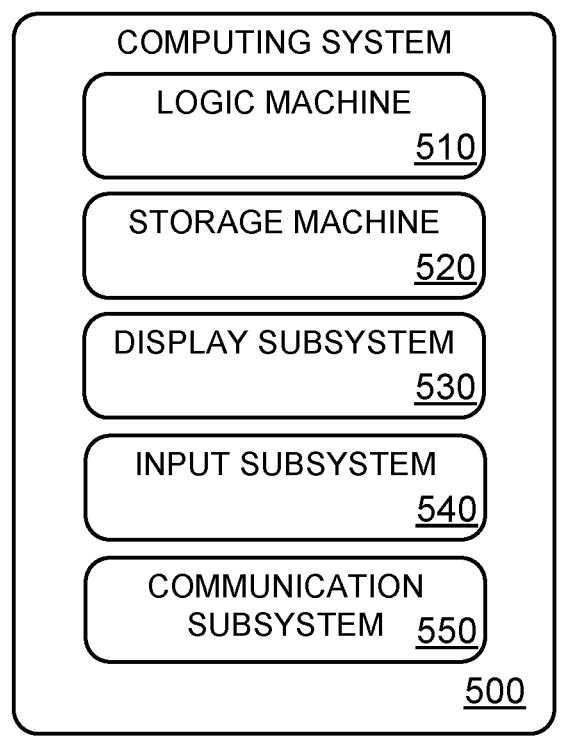
FIG. 5 schematically shows an example classical computing device.

FIG. 5 schematically shows a non-limiting embodiment of a computing system 500 that can enact one or more of the methods and processes described above. Computing system 500 is shown in simplified form. Computing system 500 may take the form of one or more personal computers, server computers, tablet computers, home-entertainment computers, network computing devices, gaming devices, mobile computing devices, mobile communication devices (e.g., smart phone), and/or other computing devices.

Computing system 500 includes a logic machine 510 and a storage machine 520. Computing system 500 may optionally include a display subsystem 530, input subsystem 540, communication subsystem 550, and/or other components not shown in FIG. 5.

Logic machine 510 includes one or more physical devices configured to execute instructions. For example, the logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic machine may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of the logic machine optionally may be distributed among two or more separate devices, which may be remotely located and/or configured for coordinated processing. Aspects of the logic machine may be virtualized and executed by remotely accessible, networked computing devices configured in a cloud-computing configuration.

Storage machine 520 includes one or more physical devices configured to hold instructions executable by the logic machine to implement the methods and processes described herein. When such methods and processes are implemented, the state of storage machine 520 may be transformed—e.g., to hold different data.

Storage machine 520 may include removable and/or built-in devices. Storage machine 520 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage machine 520 may include volatile, nonvolatile, dynamic, static, read/write, read-only, random-access, sequential-access, location-addressable, file-addressable, and/or content-addressable devices.

It will be appreciated that storage machine 520 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 510 and storage machine 520 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

When included, display subsystem 530 may be used to present a visual representation of data held by storage machine 520. This visual representation may take the form of a graphical user interface (GUI). As the herein described methods and processes change the data held by the storage machine, and thus transform the state of the storage machine, the state of display subsystem 530 may likewise be transformed to visually represent changes in the underlying data. Display subsystem 530 may include one or more display devices utilizing virtually any type of technology. Such display devices may be combined with logic machine 510 and/or storage machine 520 in a shared enclosure, or such display devices may be peripheral display devices.

When included, input subsystem 540 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 550 may be configured to communicatively couple computing system 500 with one or more other computing devices. Communication subsystem 550 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 500 to send and/or receive messages to and/or from other devices via a network such as the Internet.

In one example, enacted via execution of stored instructions on a computing device, a method for obtaining a solution to a multiproduct formula of order m to solve a quantum computing problem comprising a product formula comprises: selecting a set of exponents $k_j$, wherein each $k_j$ is a real number and is an exponent in a linear combination of product formulas; based on the set of exponents $k_j$, determining the set of pre-factors based on an underdetermined solution to an m×M system of linear equations in which the exponents are expressed as a Vandermonde matrix $V_{m,M}(k^{-\alpha}) \in \mathbb{R}^{m \times M}$ where $\alpha$ is an order of the product formula, and where M is a number of lower-order product formulas comprised in the linear combination of product formulas; and using the set of exponents $k_j$ and the set of pre-factors $a_j$ to solve the quantum computing problem comprising the product formula. In such an example, or any other example, the m×M system of linear equations is additionally or alternatively expressed as:

$$[V_{m,M}(k^{-\alpha})] \underbrace{\begin{bmatrix} a_1 \\ a_2 \\ \vdots \\ a_M \end{bmatrix}}_{\vec{a}} = \underbrace{\begin{bmatrix} 1 \\ 0 \\ \vdots \\ 0 \end{bmatrix}}_{\vec{e}_1},$$

wherein the quantum computing problem is additionally or alternatively a Hamiltonian simulation, and wherein the linear combination of product formulas is additionally or alternatively as follows:

$$U_{\vec{k}}(\Delta) = \sum_{j=1}^{M} a_j U_2^{k_j}\left(\frac{\Delta}{k_j}\right) = e^{-iH\Delta} + \mathcal{O}((N\|h\|\Delta)^{2m+2}),$$

wherein U represents the product formula, $\Delta$ is a step size, is a set of pre-factors, H is a sum of Hamiltonians h, $\mathcal{O}$ is a cost function, and N is a number of terms. In any of the preceding examples, or any other example, the linear combination of product formulas is additionally or alternatively an expression of the symmetric Trotter-Suzuki formula as follows: $U_2(\Delta) = \{\vec{U}_1(\Delta/2) \cdot \{\vec{U}(\Delta/2) = e^{-iH\Delta} + \mathcal{O}(\Delta^4)$. In any of the preceding examples, or any other example wherein $\alpha=2$, the Vandermonde matrix is additionally or alternatively as follows:

$$\underbrace{\begin{bmatrix} 1 & 1 & \cdots & 1 \\ k_1^{-2} & k_2^{-2} & \cdots & k_M^{-2} \\ \vdots & \vdots & \ddots & \vdots \\ k_1^{-2m+2} & k_2^{-2m+2} & \cdots & k_M^{-2m+2} \end{bmatrix}}_{V_{m,M}(\vec{k}^{-2})}.$$

In any of the preceding examples, or any other example wherein M=m, the underdetermined solution to the m×M system of linear equations additionally or alternatively has the solution:

$$a_j = \prod_{q=\{1,\ldots,m\}\setminus j} \frac{k_{[j]}^2}{k_j^2 - k_q^2} = \prod_{q \neq j} \frac{1}{1 - \left(\frac{k_q}{k_j}\right)^2}.$$

In any of the preceding examples, or any other example, the underdetermined solution to the m×M system of linear equations is additionally or alternatively determined based on the following linear program:

$$\min_{\vec{a}} |\vec{a}|_1 \text{ s.t. } V_{m,M}(\vec{k}^{-\alpha}) \cdot \vec{a} = \vec{e}_1 \text{ and } k_j = j.$$

In any of the preceding examples, or any other example, the underdetermined solution to the m×M system of linear equations is additionally or alternatively based on fractional queries to $U_2$, and wherein the exponents are arbitrary real numbers. In any of the preceding examples, or any other example, the underdetermined solution to the m×M system of linear equations is additionally or alternatively determined based on a fractional multiproduct wherein $V_{m,m}(\vec{x})$ is chosen such that $$x_j = \sin^2\left(\frac{\pi(2j-1)}{8m}\right) \in (0, 1/2).$$

In another example, a computing device, comprises a processor; and a storage device holding instructions that, in response to a request to obtain a solution to a multiproduct formula of order m to solve a quantum computing problem comprising a product formula, cause the processor to: select a set of exponents $k_j$, wherein each $k_j$ is a real number and is an exponent in the following linear combination of product formulas:

$$U_{\vec{k}}(\Delta) = \sum_{j=1}^{M} a_j U_2^{k_j}\left(\frac{\Delta}{k_j}\right) = e^{-iH\Delta} + \mathcal{O}((N\|h\|\Delta)^{2m+2}),$$

wherein U represents the product formula, M is a number of lower-order product formulas comprised in the linear combination of product formulas, $\Delta$ is a step size, $a_j$ is a set of pre-factors, H is sum of Hamiltonians h, $\mathcal{O}$ is a cost function, N is a number of terms; based on the set of exponents $k_j$, determine the set of pre-factors based on an underdetermined solution to the following m×M system of linear equations $$\begin{bmatrix} 1 & 1 & \cdots & 1 \\ k_1^{-2} & k_2^{-2} & \cdots & k_M^{-2} \\ \vdots & \vdots & \ddots & \vdots \\ k_1^{-2m+2} & k_2^{-2m+2} & \cdots & k_M^{-2m+2} \end{bmatrix} \begin{bmatrix} a_1 \\ a_2 \\ \vdots \\ a_M \end{bmatrix} = \begin{bmatrix} 1 \\ 0 \\ \vdots \\ 0 \end{bmatrix};$$

$$\underbrace{\phantom{XXXXXXXXXXXXXX}}_{V_{m,M}(\vec{k}^{-2})} \quad \underbrace{\phantom{XX}}_{\vec{a}} \quad \underbrace{\phantom{XX}}_{\hat{e}_1}$$

and use the set of exponents $k_j$ and the set of pre-factors $a_j$ to solve the quantum computing problem comprising the product formula. In such an example, or any other example, the linear combination of product formulas is additionally or alternatively the symmetric Trotter-Suzuki formula: $U_2(\Delta) = \{\vec{U}_1(\Delta/2) \cdot \{\bar{u}_1(\Delta/2) = e^{-iH\Delta} + O(\Delta^4)$. In any of the preceding examples, or any other example wherein M=m, the underdetermined solution to the m×M system of linear equations additionally or alternatively has the solution:

$$a_j = \prod_{q=\{1,\ldots,m\}\setminus j} \frac{k_{[j]}^2}{k_j^2 - k_q^2} = \prod_{q \neq j} \frac{1}{1 - \left(\frac{k_q}{k_j}\right)^2}.$$

In any of the preceding examples, or any other example, the underdetermined solution to the m×M system of linear equations is additionally or alternatively determined based on the following linear program:

$$\min_{\vec{a}} |\vec{a}|_1 \text{ s.t. } V_{m,M}(\vec{k}^{-2}) \cdot \vec{a} = \hat{e}_1 \text{ and } k_j = j.$$

In any of the preceding examples, or any other example, the underdetermined solution to the m×M system of linear equations is additionally or alternatively based on fractional queries to $U_2$, and the exponents are additionally or alternatively arbitrary real numbers. In any of the preceding examples, or any other example, the underdetermined solution to the m×M system of linear equations is additionally or alternatively determined based on a fractional multiproduct wherein $V_{m,m}(\vec{x})$ is additionally or alternatively chosen such that $$x_j = \sin^2\left(\frac{\pi(2j-1)}{8m}\right) \in (0, 1/2).$$

In any of the preceding examples, or any other example, the computing device is additionally or alternatively a quantum computing device further comprising: a register including a plurality of qubits; a modulator configured to implement a quantum-logic operation on the plurality of qubits according to control-parameter values stored at the storage device; and a demodulator configured to reveal data reflecting a quantum state of the plurality of qubits; and wherein the controller is operatively coupled to the modulator and to the demodulator. In any of the preceding examples, or any other example, the computing device is additionally or alternatively a classical computing device.

In yet another example, a quantum-computing device implemented method for simulating time-evolution of a Hamiltonian via a multiproduct formula of order m, comprises: selecting a set of exponents $k_j$, wherein each $k_j$ is a real number and is an exponent in the following linear combination of product formulas:

$$U_{\vec{k}}(\Delta) = \sum_{j=1}^{M} a_j U_2^{k_j}\left(\frac{\Delta}{k_j}\right) = e^{-iH\Delta} + \mathcal{O}((N\|h\|\Delta)^{2m+2});$$

wherein U represents the product formula, M is a number of lower-order product formulas comprised in the linear combination of product formulas, $\Delta$ is a step size, $a_j$ is a set of pre-factors, H is sum of Hamiltonians h, $\mathcal{O}$ is a cost function, N is a number of terms; based on the set of exponents $k_j$, determining the set of pre-factors $a_j$ based on an underdetermined solution to the following m×M system of linear equations:

$$\begin{bmatrix} 1 & 1 & \cdots & 1 \\ k_1^{-2} & k_2^{-2} & \cdots & k_M^{-2} \\ \vdots & \vdots & \ddots & \vdots \\ k_1^{-2m+2} & k_2^{-2m+2} & \cdots & k_M^{-2m+2} \end{bmatrix} \begin{bmatrix} a_1 \\ a_2 \\ \vdots \\ a_M \end{bmatrix} = \begin{bmatrix} 1 \\ 0 \\ \vdots \\ 0 \end{bmatrix},$$

$$\underbrace{\phantom{XXXXXXXXXXXXXX}}_{V_{m,M}(\vec{k}^{-2})} \quad \underbrace{\phantom{XX}}_{\vec{a}} \quad \underbrace{\phantom{XX}}_{\hat{e}_1}$$

wherein the underdetermined solution is based on the following linear program $$\min_{\vec{a}} |\vec{a}|_1 \text{ s.t. } V_{m,M}(\vec{k}^{-2}) \cdot \vec{a} = \hat{e}_1 \text{ and } k_j = j;$$

and using the set of exponents $k_j$ and the set of pre-factors $a_j$ to simulating time-evolution of the Hamiltonian. In such an example, or any other example wherein M=m, the underdetermined solution to the m×M system of linear equations additionally or alternatively has the solution:

$$a_j = \prod_{q=\{1,\ldots,m\}\setminus j} \frac{k_{[j]}^2}{k_j^2 - k_q^2} = \prod_{q \neq j} \frac{1}{1 - \left(\frac{k_q}{k_j}\right)^2}.$$

In any of the preceding examples, or any other example, the underdetermined solution to the m×M system of linear equations is additionally or alternatively based on fractional queries to $U_2$, and wherein the exponents $k_j$ are additionally or alternatively arbitrary real numbers. In any of the preceding examples, or any other example, the linear combination of product formulas is additionally or alternatively the symmetric Trotter-Suzuki formula: $U_2(\Delta) = \{\overline{U}_1(\Delta/2) \cdot \{\overleftarrow{U}(\Delta/2) = E^{-iH\Delta} + O(\Delta^4)$.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. Enacted via execution of stored instructions on a computing device, a method for obtaining a solution to a multiproduct formula of order m to solve a quantum computing problem comprising a product formula, the method comprising:
    selecting a set of exponents $k_j$, wherein each $k_j$ is a real number and is an exponent in a linear combination of product formulas;
    based on the set of exponents $k_j$, determining the set of pre-factors $a_j$ based on an underdetermined solution to an m×M system of linear equations in which the exponents are expressed as a Vandermonde matrix $V_{m,M}(k^{-\alpha}) \in \mathbb{R}^{m \times M}$, where $\alpha$ is an order of the product formula, and where M is a number of lower-order product formulas in the linear combination of product formulas; and
    using the set of exponents $k_j$ and the set of pre-factors $a_j$ to solve the quantum computing problem comprising the product formula.

2. The method of claim 1, wherein the m×M system of linear equations is expressed as:

$$[V_{m,M}(k^{-\alpha})]\underbrace{\begin{bmatrix} a_1 \\ a_2 \\ \vdots \\ a_M \end{bmatrix}}_{\vec{a}} = \underbrace{\begin{bmatrix} 1 \\ 0 \\ \vdots \\ 0 \end{bmatrix}}_{\hat{e}_1},$$

wherein the quantum computing problem is a Hamiltonian simulation, and wherein the linear combination of product formulas is as follows:

$$U_{\vec{k}}(\Delta) = \sum_{j=1}^{M} a_j U_2^{k_j}\left(\frac{\Delta}{k_j}\right) = e^{-iH\Delta} + O((N\|h\|\Delta)^{2m+2}),$$

wherein U represents the product formula, $\Delta$ is a step size, $a_j$ is a set of pre-factors, H is a sum of Hamiltonians h, $O$ is a cost function, and N is a number of terms.

3. The method of claim 2, wherein the linear combination of product formulas is an expression of the symmetric Trotter-Suzuki formula as follows:

$$U_2(\Delta) = \overrightarrow{U}_1(\Delta/2) \cdot \overleftarrow{U}_1(\Delta/2) = e^{-iH\Delta} + O(\Delta^4).$$

4. The method of claim 2, wherein $\alpha=2$, and wherein the Vandermonde matrix is as follows:

$$\underbrace{\begin{bmatrix} 1 & 1 & \cdots & 1 \\ k_1^{-2} & k_2^{-2} & \cdots & k_M^{-2} \\ \vdots & \vdots & \ddots & \vdots \\ k_1^{-2m+2} & k_2^{-2m+2} & \cdots & k_M^{-2m+2} \end{bmatrix}}_{V_{m,M}(\vec{k}^{-2})}.$$

5. The method of claim 4, wherein M=m, and wherein the underdetermined solution to the m×M system of linear equations has the solution:

$$a_j = \prod_{q=\{1,\ldots,m\}\setminus j} \frac{k_{[[j],j[[j]]}^2}{k_j^2 - k_q^2} = \Pi_{q \neq j} \frac{1}{1 - \left(\frac{k_q}{k_j}\right)^2}.$$

6. The method of claim 1, wherein the underdetermined solution to the m×M system of linear equations is determined based on the following linear program:

$$\min_{\vec{a}} \perp |\vec{a}| \perp_1 \text{ s.t. } V_{m,M}(\vec{k}^{-\alpha}) \cdot \vec{a} = \hat{e}_1 \text{ and } k_j = j.$$

7. The method of claim 6, wherein the underdetermined solution to the m×M system of linear equations is based on fractional queries to $U_2$, and wherein the exponents $k_j$ are arbitrary real numbers.

8. The method of claim 6, wherein the underdetermined solution to the m×M system of linear equations is determined based on a fractional multiproduct wherein $V_{m,m}(\vec{x})$ is chosen such that $$x_j = \sin^2\left(\frac{\pi(2j-1)}{8m}\right) \in (0, 1/2).$$

9. A computing device, comprising:
    a processor; and
    a storage device holding instructions that, in response to a request to obtain a solution to a multiproduct formula of order m to solve a quantum computing problem comprising a product formula, cause the processor to:
    select a set of exponents $k_j$, wherein each $k_j$ is a real number and is an exponent in the following linear combination of product formulas:

$$U_{\vec{k}}(\Delta) = \sum_{j=1}^{M} a_j U_2^{k_j}\left(\frac{\Delta}{k_j}\right) = e^{-iH\Delta} + \mathcal{O}((N\|h\|\Delta)^{2m+2}),$$

wherein U represents the product formula, M is a number of lower-order product formulas comprised in the linear combination of product formulas, $\Delta$ is a step size, $a_j$ is a set of pre-factors, H is sum of Hamiltonians h, $\mathcal{O}$ is a cost function, N is a number of terms;

based on the set of exponents $k_j$, determine the set of pre-factors $a_j$ based on an underdetermined solution to the following m×M system of linear equations:

$$\underbrace{\begin{bmatrix} 1 & 1 & \cdots & 1 \\ k_1^{-2} & k_2^{-2} & \cdots & k_M^{-2} \\ \vdots & \vdots & \ddots & \vdots \\ k_1^{-2m+2} & k_2^{-2m+2} & \cdots & k_M^{-2m+2} \end{bmatrix}}_{V_{m,M}(\vec{k}^{-2})} \underbrace{\begin{bmatrix} a_1 \\ a_2 \\ \vdots \\ a_M \end{bmatrix}}_{\vec{a}} = \underbrace{\begin{bmatrix} 1 \\ 0 \\ \vdots \\ 0 \end{bmatrix}}_{\vec{e_1}}; \text{ and}$$

use the set of exponents $k_j$ and the set of pre-factors $a_j$ to solve the quantum computing problem comprising the product formula.

10. The computing device of claim 9, wherein the linear combination of product formulas is the symmetric Trotter-Suzuki formula:

$$U_2(\Delta) = \overleftarrow{U}_1(\Delta/2) \cdot \overrightarrow{U}_1(\Delta/2) = e^{-iH\Delta} + \mathcal{O}(\Delta^4).$$

11. The computing device of claim 9, wherein M=m, and wherein the underdetermined solution to the m×M system of linear equations has the solution:

$$a_j = \prod_{q=\{1,\ldots,m\}\setminus j} \frac{k_{[[1]]j[[1]]}^2}{k_j^2 - k_q^2} = \Pi_{q \neq j} \frac{1}{1-\left(\frac{k_q}{k_j}\right)^2}.$$

12. The computing device of claim 11, wherein the underdetermined solution to the m×M system of linear equations is determined based on the following linear program:

$$\min_{\vec{a}} \perp |\vec{a}| \perp_1 \text{ s.t.} V_{m,M}(\vec{k}^{-\alpha}) \cdot \vec{a} = \vec{e_1} \text{ and } k_j = j.$$

13. The computing device of claim 11, wherein the underdetermined solution to the m×M system of linear equations is based on fractional queries to $U_2$, and wherein the exponents $k_j$ are arbitrary real numbers.

14. The computing device of claim 11, wherein the underdetermined solution to the m×M system of linear equations is determined based on a fractional multiproduct wherein $V_{m,m}(\vec{x})$ is chosen such that $$x_j = \sin^2\left(\frac{\pi(2j-1)}{8m}\right) \in (0, 1/2).$$

15. The computing device of claim 9, wherein the computing device is a quantum computing device further comprising:

a register including a plurality of qubits;

a modulator configured to implement a quantum-logic operation on the plurality of qubits according to control-parameter values stored at the storage device; and a demodulator configured to reveal data reflecting a quantum state of the plurality of qubits; and wherein the controller is operatively coupled to the modulator and to the demodulator.

16. The computing device of claim 9, wherein the computing device is a classical computing device.

17. A quantum-computing device implemented method for simulating time-evolution of a Hamiltonian via a multiproduct formula of order m, comprising:

selecting a set of exponents $k_j$, wherein each $k_j$ is a real number and is an exponent in the following linear combination of product formulas:

$$U_{\vec{k}}(\Delta) = \sum_{j=1}^{M} a_j U_2^{k_j}\left(\frac{\Delta}{k_j}\right) = e^{-iH\Delta} + \mathcal{O}((N\|h\|\Delta)^{2m+2});$$

wherein U represents the product formula, M is a number of lower-order product formulas comprised in the linear combination of product formulas, $\Delta$ is a step size, $a_j$ is a set of pre-factors, H is sum of Hamiltonians h, $\mathcal{O}$ is a cost function, N is a number of terms;

based on the set of exponents $k_j$, determining the set of pre-factors $a_j$ based on an underdetermined solution to the following m×M system of linear equations:

$$\underbrace{\begin{bmatrix} 1 & 1 & \cdots & 1 \\ k_1^{-2} & k_2^{-2} & \cdots & k_M^{-2} \\ \vdots & \vdots & \ddots & \vdots \\ k_1^{-2m+2} & k_2^{-2m+2} & \cdots & k_M^{-2m+2} \end{bmatrix}}_{V_{m,M}(\vec{k}^{-2})} \underbrace{\begin{bmatrix} a_1 \\ a_2 \\ \vdots \\ a_M \end{bmatrix}}_{\vec{a}} = \underbrace{\begin{bmatrix} 1 \\ 0 \\ \vdots \\ 0 \end{bmatrix}}_{\vec{e_1}},$$

wherein the underdetermined solution is based on the following linear program:

$$\min_{\vec{a}} \perp |\vec{a}| \perp_1 \text{ s.t.} V_{m,M}(\vec{k}^{-\alpha}) \cdot \vec{a} = \vec{e_1} \text{ and } k_j = j; \text{ and}$$

using the set of exponents $k_j$ and the set of pre-factors $a_j$ to simulating time-evolution of the Hamiltonian.

18. The quantum-computing device implemented method of claim 17, wherein M=m, and wherein the underdetermined solution to the m×M system of linear equations has the solution:

$$a_j = \prod_{q=\{1,\ldots,m\}\setminus j} \frac{k_{[[1]]j[[1]]}^2}{k_j^2 - k_q^2} = \Pi_{q \neq j} \frac{1}{1-\left(\frac{k_q}{k_j}\right)^2}.$$

19. The quantum-computing device implemented method of claim 18, wherein the underdetermined solution to the m×M system of linear equations is based on fractional queries to $U_2$, and wherein the exponents $k_j$ are arbitrary real numbers.

20. The quantum-computing device implemented method of claim 17, wherein the linear combination of product formulas is the symmetric Trotter-Suzuki formula:

$$U_2(\Delta) = \vec{U}_1(\Delta/2) \cdot \overleftarrow{U}_1(\Delta/2) = e^{-iH\Delta} + O(\Delta^4).$$

* * * * *